US011013257B2

(12) United States Patent
Meusel et al.

(10) Patent No.: US 11,013,257 B2
(45) Date of Patent: May 25, 2021

(54) MARKED FILTER PAPER FOR USE AS TEST SUBSTRATE IN STANDARDIZED METHODS FOR EVALUATION OF THE IGNITION PROPENSITY OF CIGARETTES

(71) Applicant: AXAGARIUS GMBH & CO. KG, Düren (DE)

(72) Inventors: Markus Meusel, Würselen (DE); Christian Prokisch, Düren (DE)

(73) Assignee: AXAGARIUS GMBH & CO. KG, Düren (DE)

( * ) Notice: Subject to any disclaimer, the term of this patent is extended or adjusted under 35 U.S.C. 154(b) by 510 days.

(21) Appl. No.: 15/745,518

(22) PCT Filed: Oct. 21, 2016

(86) PCT No.: PCT/EP2016/075409
§ 371 (c)(1),
(2) Date: Jan. 17, 2018

(87) PCT Pub. No.: WO2017/072045
PCT Pub. Date: May 4, 2017

(65) Prior Publication Data
US 2018/0228207 A1    Aug. 16, 2018

(30) Foreign Application Priority Data
Oct. 30, 2015    (DE) .......................... 102015118595.4

(51) Int. Cl.
*A24C 5/34*    (2006.01)
*D21H 27/08*    (2006.01)
(Continued)

(52) U.S. Cl.
CPC .............. *A24C 5/34* (2013.01); *D21H 27/00* (2013.01); *D21H 27/08* (2013.01); *G01N 25/00* (2013.01); *G01N 33/34* (2013.01)

(58) Field of Classification Search
None
See application file for complete search history.

(56) References Cited

U.S. PATENT DOCUMENTS

| 5,030,263 | A  | 7/1991  | Kemp   |
| 8,863,757 | B2 | 10/2014 | Kraker |

(Continued)

FOREIGN PATENT DOCUMENTS

| DE | 608187 C       | 1/1935 |
| DE | 68918387 T2    | 1/1995 |
| DE | 202006016075 U1| 2/2007 |

OTHER PUBLICATIONS

Olhemiller et al.,"Test Methods for Quantifying the Propensity of Cigarettes to Ignite Soft Furnishings", v 2, NIST Spec Pub 851-2, U.S. Dept. Commerce,176 pages, [online],retr from the Internet,[retr. Oct. 20, 2020], URL:https://nvlpubs.nist.gov/nistpubs/Legacy/SP/nistspecnistspecialpublication851-2.pdf. (Year: 1993).*
(Continued)

*Primary Examiner* — Dennis R Cordray
(74) *Attorney, Agent, or Firm* — Faegre Drinker Biddle & Reath LLP (57) ABSTRACT

The present invention relates to a cellulose filter paper for testing the ignition propensity of cigarette paper that is provided with a marking with which the rough surface of the filter paper can be distinguished from the smooth surface, and a method for its production, a method for testing the ignition propensity of cigarette paper, and a kit having a plurality of such filter papers or stacks of such filter papers.

19 Claims, 8 Drawing Sheets

(51) Int. Cl.
*G01N 25/00* (2006.01)
*G01N 33/34* (2006.01)
*D21H 27/00* (2006.01)

(56) References Cited

U.S. PATENT DOCUMENTS

| | | | |
|---|---|---|---|
| 2002/0056535 A1 | 5/2002 | Hama et al. | |
| 2005/0056293 A1* | 3/2005 | Zawadzki | C07D 219/06 |
| | | | 131/365 |
| 2012/0305012 A1* | 12/2012 | Dyakonov | A24D 1/025 |
| | | | 131/284 |
| 2014/0322488 A1 | 10/2014 | Tirimacco | |

OTHER PUBLICATIONS

English Translation of International Preliminary Report On Patentability for International Application No. PCT/EP2016/075409, dated May 3, 2018.
International Search Report for PCT/EP2016/075409 dated Dec. 14, 2016.
Written Opinion of the International Searching Authority for PCT/EP2016/075409 dated Dec. 14, 2016.

* cited by examiner

MARKED FILTER PAPER FOR USE AS TEST SUBSTRATE IN STANDARDIZED METHODS FOR EVALUATION OF THE IGNITION PROPENSITY OF CIGARETTES

CROSS-REFERENCE TO RELATED APPLICATIONS

This application is a national stage application (under 35 U.S.C. § 371) of PCT/EP2016/075409, filed Oct. 21, 2016, which claims benefit of German Application No. 102015118595.4, filed Oct. 30, 2015, both of which are incorporated herein by reference in their entirety.

The present invention relates to a cellulose filter paper for testing the ignition propensity of cigarette paper, a method for its production, a method for testing the ignition propensity of cigarette paper, and a kit having a plurality of such filter papers or stacks of such filter papers.

According to the EU Commission, unattended, smoldering cigarettes are the leading cause of fires resulting in death in Europe. According to information provided by the EU Member States for the years 2003 to 2008, each year 30,000 fires were caused by cigarettes in the EU. As a result, more than 1,000 people have died and more than 4,000 have been injured.

There is therefore an urgent need to reduce hazards caused by cigarettes. One starting point is the cigarette itself. Thus, since November 2011, only so-called fire-safe cigarettes may be sold in the European Union. These cigarettes, which have already been used in the US, Canada, or Australia for many years, have a reduced ignition propensity effected by a change in the cigarette paper. The cigarette paper is modified by annular bands in 2 to 3 areas that are not recognized by the naked eye. When the glow reaches such a band, less oxygen is available and the burning process is reduced. The cigarette can then self-extinguish. U.S. Pat. No. 8,863,757 can be named as an example from this technological area.

The manufacture and testing of such cigarettes with reduced ignition propensity is subject to strict safety standards. For example, DIN EN ISO 12863 (standard test method for assessing the ignition propensity of cigarettes) defines standard test methods.

This test method determines the probability of whether a cigarette arranged on a heat-absorbing substrate generates sufficient heat to continue burning along the length of the tobacco column and thus may cause a fire. As a substrate, the standard defines a "horizontal surface consisting of layers of filter paper on which a test cigarette is placed." Specifically, the standard describes round cellulose filters having a diameter of 15 cm, and the weight of the filter is also specified. As a standard, a set (stack) of 10 individual filters is used as the substrate.

In order to achieve standardized, uniform conditions during the standard test, it is necessary to position the rough upper side of the filter papers upward.

This standard requirement is very difficult to implement for the user of the method. While the roughness of such a filter surface can be tested and determined using technical measuring equipment (machine-technical), it is nearly impossible to implement in practice. Therefore, in daily practice the roughness is determined on a purely haptic basis by the user. The asymmetry of the filter papers with a smoother and a rougher side is a result of the production process, however, in individual cases, the differences between the sides are very difficult to assess even by the experienced expert. Which side of the paper has the higher roughness depends mainly on the production method. Thus, during the production of filter paper, the wire-side surface of the filter paper can be the rougher surface, but there are also processes in which the wire-side defines the smoother side of the later paper.

A measuring method for determining the roughness is, for example, available according to DIN 53108:1995-01. This standard describes the determination of the roughness according to Bendtsen. Here, the roughness is the volume of airflow that passes between the measuring ring of the measuring head of the Bendtsen apparatus and the sample surface, and that is created at a set positive pressure. The measurement of roughness according to this standardized procedure is laborious and requires a special measuring apparatus.

According to its provisions, the standard procedure for ignitability requires that the rough side of the filter paper faces upward. The rough side must therefore be determined prior to being introduced into the measuring chamber. In principle, this can be done before or after preconditioning the paper (preconditioning by incubating the paper at a defined temperature and humidity), conveniently, however, this is done before preconditioning since the preconditioned filter paper must be inserted directly into the test apparatus in order to determine the ignitability.

Such a method for testing the ignition propensity of cigarette paper generally comprises the steps of:
a) Preconditioning a round cellulose filter paper having a rough and a smooth surface;
b) Horizontally placing the pre-conditioned filter paper onto a substrate holder (7), whereby the rough surface of the filter paper faces upward,
c) Subsequently placing a metal ring (11) onto the filter paper, whereby the metal ring (11) has two metal pins (12) spaced in parallel to each other for fixing an ignited cigarette that protrude into the interior of the ring and have a spacing to each other and a length that allows the unlit end of a cigarette to be fixed;
d) Subsequently placing a cigarette ignited at one end, with the seam of the cigarette paper facing upward, onto the rough surface of the filter paper, whereby the non-lit end of the cigarette is fixed between metal pins (12) and
e) Determining the burning behavior of the cigarette.

Figure 3:
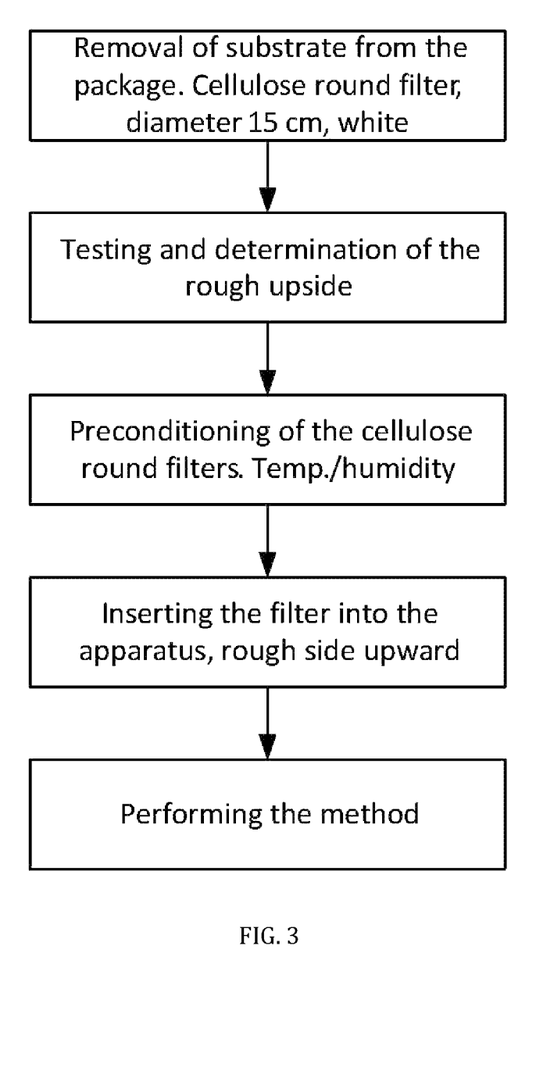

An overview of the method steps for determining the ignition propensity of cigarettes by the user is shown in FIG. 3. The prior art has the above-mentioned disadvantage that the orientation of the filter paper used as a substrate must be determined before performing the test. Haptic testing is unreliable and can lead to errors. In addition to uncertainties in the test results, it can ultimately result in far-reaching liability-related consequences. However, instrumented testing of the roughness of surfaces is generally too time consuming.

The object of the present invention is to provide an improved method for testing the ignition propensity of cigarette paper that enables a simple yet error-free identification of the smooth or rough side of a filter paper for assessing the ignition propensity of cigarettes and without the use of a test apparatus.

The object is achieved with the method of the aforementioned type in that a marked cellulose filter paper is used in which the marking allows a simple and clear distinction between the rough and the smooth surface of the cellulose filter paper, advantageously by means of haptic testing and/or by viewing by the test personnel.

The present invention therefore relates to a cellulose filter paper to check the ignition propensity of the cigarette paper that is characterized in that the filter paper is provided with a marking with which the smooth surface of the filter paper can be distinguished from the rough surface.

For this purpose, the cellulose filters are marked during or after the paper production in a way that allows a simple and unambiguous assignment into (rougher) upside and (smoother) underside.

Accordingly, a further object of the present invention is a method for producing a cellulose filter paper according to the invention in which the filter paper is provided with a marking with which the rough surface of the filter paper can be distinguished from the smooth surface.

In principle, a variety of technical options are available to mark paper or filters. For example, a watermark, a semi-fragile watermark, embossing, printing and/or punching may be mentioned as a non-exhaustive list.

The marking is positioned in particular outside of the center point of the filter paper, preferably in an edge region of the filter paper. This is advantageous, because it ensures that the marking does not affect the burning behavior of a cigarette that is positioned during the test, or respectively the filter paper has homogeneous properties in the area that is in contact with the cigarette.

The marking is preferably selected such that it allows to discriminate between the rough and the smooth surface of the filter paper by means of haptic testing and/or via the (normal-sighted) human eye, i.e., the marking allows test personnel to distinguish the rough side of the filter paper from the smooth side without special training and without additional aids.

The marking of the filter paper can thereby, for example, mark the rough surface of the filter paper so that the personnel knows that this side must be positioned facing upward for the test procedure. Since for the test the stacks must also be assembled with the rough side facing upward, this has certain advantages for the workflow. Naturally, the smooth side of the filter paper can also be marked.

For example, an asymmetrical symbol can preferably be used as marking, whereby the marking comprises or consists of in particular at least two geometric symbols, which preferably differ in their shape, color and/or size from each other. An asymmetrical symbol is preferred when the marking is visible on both sides of the filter paper. Such marking may comprise, for example, an arrow and a dot (e.g., ) arranged vertically or diagonally to a through the circle center of the round filter. The marking can then be seen both from the upside as well as from the underside, but the orientation of the arrow (e.g., to the left of the dot) can be assigned to the upside of the paper. If they were, however, arranged on the line projecting through the circle center of the round filter, there would be no difference between the upside and the underside of the filter paper.

A watermark presents a possibility of introducing a marking during paper production, which is e.g., incorporated in the wire section of a paper machine. When true watermarks are used, the paper web is thinned or thickened on the wire section by a fixed-position rotating roller. Letterings such as "rough," "upside," or "top" and/or individual, optionally asymmetrical symbols can be used. With this method of marking, it is not mandatorily required to predetermine the rough and less rough side of the paper web that is being formed, because the two different surfaces are already defined as a result of the manufacturing process for the paper web.

As an alternative to marking using watermarks, semi-fragile watermarks can be formed by pressing them into the much drier paper web after it has left the wire section. In this case as well, a suitable design of the watermark allows to easily later distinguish between the asymmetrical sides in the paper. With this method of marking, it is also not mandatorily required to predetermine the rough and less rough side of the paper web that is being formed, because the two different surfaces are already defined as a result of the manufacturing process for the paper web.

Particularly in view of the later cutting of paper webs, when these and other methods are used where the cutting is carried out after the markings have been applied, care should be taken that the markings are applied to the surface of the paper web in such a manner that after the paper web is cut into smaller segments, e.g., circles (round filter), they are visible on each of the segments formed.

The marking can also be provided by applying an embossing. During embossing, pressure is applied to the surface of a cellulose filter paper by a forming tool, which causes a deformation on the paper surface to create a relief. Here, too, asymmetric shapes, patterns, or letterings can be impressed, which allow to identify the upside. Preferably, the embossing is carried out in the dry paper web after it has left the wire section, so that the rougher surface is known as a result of the production process. It is not necessarily required here to determine the roughness of both surfaces of the paper web, but it can be performed for safety reasons at any time. The advantage here is that with a paper reel, the rough side needs to be determined only once in order to ensure the orientation of several thousands of filter papers.

A further possibility for producing a marking is provided by punching into the dry paper web after it has left the wire section. Suitable punching allows to mark the rougher side either by lettering such as "upside" (the lettering would be visible only in mirror writing on the smoother "underside"), or the rough side with a preferably asymmetrical symbol or an arrangement comprising at least two different symbols of different sizes and/or of different shapes.

Applying a marking by means of printing is also possible, e.g., a lettering or at least one character (symmetrical or asymmetrical, single-colored or multi-colored) or at least two different symbols. The symbols can differ, for example, in their size, shape and/or color.

In one embodiment of the present invention, the marking can be applied during the manufacturing process of the paper, on the level of the reel material, the cut sheets, or on the level of the punched or cut finished filter papers.

Insofar, according to a first embodiment of the inventive method for producing the filter paper according to the invention, the filter paper is marked during production on the wire side of the wire section, for example, by means of a true watermark. The watermarks are expediently arranged in such a manner that after passing through the entire production process up to the finished round filter paper they are arranged at the desired location of each individual filter paper.

According to a second embodiment of the inventive method for producing the filter paper according to the invention, the filter paper is delivered as reel material for the marking process. When reel material is used, the position of the rough surface is already known, either as a result of the production process or it can be determined once for the entire reel using a measurement method, for example according to DIN 53108:1995-01 (January 1995), so that the orientation is known for the further production process. The marking is then applied onto the reel material, for example, by punching, embossing, or printing at those positions at which the marking is later desired in the finished round filter. The marked reel material can subsequently be cut into sheets out of which the round filters can then be punched.

Typically, in a first step sheets are cut from the paper produced from reel material that is then punched/cut in a further step to the required shapes and dimensions (final size, e.g., 15 cm round filter).

Preferably, the reel material is cut into sheets in a manner such that the orientation of the rougher surface of the sheets is still known from the reel-up of the filter paper during production, so that an additional measurement of the surface roughness is not required in order to ensure the correct marking of the rough surface of the filter paper.

However, to be on the safe side, before marking the rough surface of a filter paper sheet, the roughness of the two surfaces of the filter paper can be determined again. The markings are then positioned such that after a sheet has been punched to the final dimension of a filter paper, the marking is arranged at the desired point on each final dimension.

Thus, according to a third embodiment of the inventive method for producing the filter paper according to the invention, the marking is performed after the reel material has been cut into sheets. In this case as well, the position of the rough surface is either known from the production process or can be determined for the entire reel before it is cut into sheets. If sheets are delivered, the rough surface can also be determined individually for each sheet, for example according to DIN 53108:1995-01 (January 1995). The respective markings can be applied to the sheets by punching, embossing, or printing at the desired position on the round filters that are subsequently generated. The round filters can then be punched out of the sheets and packaged.

The marking can also be applied during or after the sheets are punched or cut to the desired final dimensions of the segments. Here, too, the reel material is preferably cut into sheets and the subsequent punching of the sheets to the desired final dimension of a filter paper is performed such that the orientation of the rougher surface of the final dimensions is still known from the reel-up of the filter paper during production so that a further measurement of the surface roughness does not have to be performed in order to ensure a mark on the rougher surface of the filter paper.

Thus, according to a fourth embodiment of the inventive method for producing the filter paper according to the invention, the filter papers are marked after they have been punched out of the sheets. In this case as well, the position of the rough side of the reel material delivered during the production process is known either prior to production or it can be previously determined based on a single test for the entire paper reel, for example according to DIN 53108:1995-01 (January 1995). The punched round filters can be marked by punching, embossing, or printing. Since the position of the rough surface is known throughout the entire production process, it is not necessary in this case to determine the rough surface of each round filter prior to applying the marking. Applying the marking onto punched round filters has the advantage that the positions of the marking(s) can be defined with a higher precision than with the other aforementioned methods.

If necessary, the roughness of the two surfaces of a filter paper is determined as described above, preferably by a method according to DIN 53108:1995-01 (January 1995). This standard describes the determination of the roughness according to Bendtsen. Here, the roughness is the volume of airflow that passes between the measuring ring of the measuring head of the Bendtsen apparatus and the sample surface, and that is created at a set positive pressure.

As a standardized method for determining the ignitability of cigarettes is used, it is expedient to preferably apply the marking on a round filter consisting of cellulose filter paper within a 1.5 cm wide strip from the edge of the round filter, more preferably on a 1.2 cm wide strip, most preferably on a 1 cm wide strip so that the test substrate (the filter paper, preferably a round filter) on which the cigarette rests is not affected.

The filter paper is preferable a single-layer round filter having a diameter in the range of from 130 mm to 170 mm, in particular of (150±10) mm, more preferably a round filter having a diameter of (150±5) mm, most preferably a diameter in the range of (150±2) mm.

The marking of the rougher surface can for one be applied by a marking on the rougher surface, whereby said marking is visible only on the rougher side of the filter paper and not on the smoother side (e.g., by watermark, embossment, or print). In this way, the rough side is immediately identifiable. Such marked filter paper is preferably provided with a string of letters which allows an immediate allocation (such as e.g., "rough," "rough side," "upside" or the like), or a filter paper marked in this way is supplied with the information denoting (e.g., by a watermark or a print) that the marked surface of a filter paper is the rougher surface of the filter paper. This information may be supplied in the form of a digital medium, a written note etc.

Alternatively, a marking may be visible on both sides of the filter paper, e.g., by watermark, embossing, print or punch. In this way, the skilled person can also directly receive the information about which of the two sides of a filter paper is the side with the rougher surface and which is the side with the smoother surface. This can, e.g., be accomplished in form of lettering denoting, for example, "rough side" or "upside" on the rougher side, which can only be read correctly if the skilled person views the corresponding rougher side of a filter paper. If, however, the lettering is viewed from the smoother side, the lettering appears as a mirror image. Thus, when punched lettering, e.g., "upside" or "rough" is used, no further information is necessary, as the skilled person is directly able to determine the correct orientation/roughness of the filter paper on the basis of legibility/illegibility. If a print is used, the smooth side can be marked, for example, with "underside" or "smooth."

A single, in particular asymmetrical symbol, or its orientation, that is not positioned at the center of a filter paper surface may be sufficient to allow an easy distinction between the rougher and the smoother surface of a filter paper. Preferably, such a symbol is located entirely within a 1.5 cm wide strip from the edge of the circular filter, more preferably within a 1.2 cm wide strip, most preferably within a 1 cm wide strip so that the test substrate (the filter paper, preferably a round filter) on which the cigarette rests is not affected.

An asymmetrical symbol is, for example, understood as meaning a symbol that does not have a mirror symmetry about a vertical mirror plane projecting through the symbol and the center point of the round filter.

In the case of a circular filter having an asymmetrical symbol as marking, the marking must indicate which orientation of the asymmetrical symbol to the nearest edge of the filter paper defines the rougher (and thus conversely the smoother) surface of a filter paper. This information is preferably provided in the form of an image on the rougher surface with the orientation of the asymmetrical symbol on the round filter together with the indication that this presents the view of the rougher (or smoother) surface side of a round filter, for example, as an information sheet or electronically. An asymmetrical symbol can be, e.g., an arrow or a triangle.

The same conditions for a rectangular filter apply as for a round filter, but here the asymmetry of the symbol is naturally not determined by the radius, i.e., the line projecting through the circle center, but by the perpendicular line projecting to the edge of the filter paper that runs through the center of the punched symbol.

In the case of a round filter having two or more geometric symbols as markings, at least two or all of them preferably differ from each other. In order to allow a discrimination between the rough and the smooth surface of the filter paper in this embodiment, the two symbols may be arranged to each other in such a manner that the centers of both symbols do not lie on an imaginary line from the center to the edge region of the filter paper so that the two sides can be distinguished if both symbols can be seen from both sides. Preferably, the two symbols are spaced maximally 2 cm apart from each other and are each positioned maximally 1.5 cm, preferably not more than 1 cm from the edge region of a filter paper.

More preferably, this information is provided in the form of an image of the rougher surface of a round filter with the two symbols arranged on the round filter together with an indication that this presents the view of the rougher surface side of a round filter. Thus, for example, the corresponding explanation can be provided on an image enclosed as an information sheet or a file. The same requirements for determining the rough surface side of a round filter apply for a rectangular filter.

A punched symbol can be punched out directly at the edge region of the filter paper, or at least at a distance of 0.5 mm, preferably of at least 1 mm, more preferably of at least 2 mm from the edge region of the filter paper. Preferably, the punch of a symbol for marking a rough or a smoother surface of a filter paper is at least at a distance of 0.5 mm from the edge region and at a maximum of 1.5 cm from the edge area of a circular filter. If several punched symbols are used, the aforementioned values apply accordingly.

Preferably, the maximum length and the maximum width of a punched-out symbol are maximally 1.4 cm, more preferably maximally 0.8 cm independently of one another.

Another object of the present invention relates to a method for checking the ignition propensity of cigarette paper comprising the steps:
  a) Preconditioning a round cellulose filter paper having a rough and a smooth surface;
  b) Horizontally placing the pre-conditioned filter paper onto a substrate holder (7), whereby the rough surface of the filter paper faces upward,
  c) Subsequently placing a metal ring (11) on the filter paper, whereby the metal ring has two metal pins (12) spaced apart in parallel to each other for fixing an ignited cigarette, which protrude into the interior of the ring and have a spacing to each other and a length that allow to fix the unlit end of a cigarette;
  d) Subsequently placing a cigarette ignited at one end of with the seam of the cigarette wrapper facing upward on the rough surface of the filter paper, whereby the non-lit end of the cigarette is fixed between the metallic pins (12) and
  e) Determining the burning behavior of the cigarette, wherein the method is characterized in that the filter paper is a cellulose filter paper according to the invention, i.e., a filter paper provided with a marking with which the smooth surface of the filter paper can be distinguished from the rough surface.

A rectangular test chamber made of a rigid, transparent material with a smoke ventilator mounted centrally on the chamber top is usually used for the inventive testing method. The dimensions of this chamber are preferably (340±25) mm height, (292±6) mm width and (394±6) mm depth. The dimensions of the smoke ventilator are preferably (165±13) mm height and (152±6) mm inner diameter.

In the test chamber, a removable substrate holder of cylindrical design is provided for the filter paper and the cigarette to be tested. Preferably, the substrate holder has dimensions adjusted to the size of cigarettes. Typically, the substrate holder has an outer diameter of 165±1 mm, an inner diameter of 127±1 mm, and thus a wall thickness of approximately 38 mm. The height is approximately 50±1 mm. At its upper edge, the substrate holder has a circumferential step tapering toward the inside with a depth of 10±2.5 mm. The step is concentrically arranged and has a diameter of 152±1 mm. In this way, a stair-like protrusion is formed, the deeper area of which serves as a peripheral edge-side support for the filter paper. The circumferential support has a depth of approximately 25 mm.

In order to fix the filter paper or the stack of filter papers, a metal ring is provided which is placed from above onto the edge of the filter paper that is placed in the holder. The metal ring has an outer diameter that is smaller than the inner diameter of the step, i.e., approximately 150±1 mm in the present case. The inner diameter of the ring is expediently selected such that after being positioned, the metal ring is at most flush with the inner wall of the substrate holder, however, the inner diameter is preferably greater so that the metal ring recoils circumferentially from the inner wall of the substrate holder, i.e., for example, 130'±1 mm. The material thickness of the metal ring is approximately 6.4±1 mm.

The metal ring preferably consists of a metal having a high specific weight, i.e., for example, with a density of 8,550±150 kg*m−3, preferably of brass, so that the filter paper sheets are pressed flat against one another by the weight of the metal ring. The mass of the metal ring is, for example 235 g to 295 g.

In a lateral sectional view two metal pins spaced apart in parallel direction from each other are embedded in the metal ring, which protrude approximately 17±1 mm into the interior of the metal ring. The metal pins are positioned such that an imaginary line projecting centrally and in parallel to the metal pins project through the center of the metal ring. The spacing of the metal pins to each other is selected such that a cigarette that is inserted between the pins is prevented from rolling away to the side, i.e., is fixed. A conventional cigarette with a diameter of 8 mm has metal pins that are spaced approximately 8.1±1 mm apart.

Preferably, the bottom of the substrate holder is positioned 20±1 mm above the bottom of the aforementioned test chamber. In this way, it can be ensured that there is sufficient ventilation underneath the inserted filter paper as well. This distance can be realized, for example, by three or four feet that serve as spacers and are fixed to the bottom side of the substrate holder in preferably identical radial intervals. The feet may instead also be firmly connected to the test chamber at the appropriate positions.

According to a preferred further development of the aforementioned testing method, the results of step e) are analyzed according to the following criteria:
  A) Complete burning of the cigarette;
  B) Incomplete burning of the cigarette.

Thereby A) means that when filter cigarettes are used a cigarette continues to burn until the front edge of the tipping paper is reached, or when cigarettes without filter are used until the metal pins are reached, and B) means that when filter cigarettes are used the cigarette extinguishes before the front edge of the tipping paper is reached or when cigarettes without filter are used before the metal pins are reached.

To improve the significance of the tests, it may be provided to repeat the testing process with a variety of cigarettes of the same type, i.e., in particular having the same cigarette paper. Accordingly, the process may preferably comprise the following additional steps:

f) At least 39 repetitions of steps a) to e) and
g) Determining the proportion of the at least 40 tests in which the result was A).

In the testing process a single filter paper for supporting the lighted cigarette can in principle be used, whereby preferably a stack with a defined number of pieces of the same filter paper is used. In such a method, a plurality of filter papers can thus be preconditioned in step a), and in step b) a stack of the preconditioned filter papers are placed on the substrate holder, whereby the rough surfaces of the filter papers of the stack face upward and the stack comprises at least 3, in particular 10 or 15 filter papers. More preferably, the at least 40 tests are performed once each with a stack of 10 and thereafter with stacks of 3 and 15 filter papers each in order to determine the burning behavior in relation to the number of layers of filter paper.

The test cigarette is typically marked before it is lit at 5±1 mm and 15±1 mm from the end of cigarettes to be lit, for example with a pencil or another marking device. Subsequently, the cigarette is lit and only then placed on the rough surface of the fixed filter paper or on the filter paper stack when the glow reaches the 15±1 mm mark relative to the lit end of the cigarette.

The analysis of step e) is preferably carried out with a higher level of detail. To this end, in addition to the results A) (complete burn-off)—and B) (incomplete burn-off), the other two results C) and D) are investigated, where C) Self-extinguishing is evaluated as A) if after being lit the cigarette extinguishes before the 15±1 mm mark of the cigarette extending from the end of the cigarette to be lit is reached, with the notation that this occurred before being placed onto the rough surface of the cellulose filter paper;
D) If the smoke of the burning cigarette is not laminar even after the chamber and the ventilation system were checked, this result is noted.

Preferably, in the method according to the invention, each cigarette used for the test is preconditioned before being lit by storing the cigarette for at least 24 h before the test in an environment with a relative humidity of 55±5% and a temperature of 23±3° C. This can compensate for variations in the burning behavior that might result from a possible different prestorage.

The preconditioning or the filter paper(s) is, for example, performed in such a way that a 100-sheet box containing marked filter paper is stored with an open lid for at least seven days (7*24 h) before the test in an environment with a relative humidity of 55±5% and a temperature of 23±3° C. Alternatively, if filter paper stacks are used, corresponding sets, i.e., stacks of 3, 10 or 15 marked filter papers can be stored for at least 8 h before the test in an environment with a relative humidity of 55±5% and a temperature of 23±3° C. More preferably, sets with 15 marked filter papers are used that are stored for at least 8 h before the test in an environment with a relative humidity of 55±5% and a temperature of 23±3° C.

A further preferred embodiment relates to an inventive method in which the mean mass and the standard deviation of 5 sets comprising 15 sheets each of the conditioned marked filter paper is 26.1±0.5 g, whereby the standard deviation of the five weighings is no greater than 0.3 g.

A further preferred embodiment relates to an inventive method in which the average mass of 5 sets comprising 15 marked and dried filter papers is 24.7±0.5 g, whereby the standard deviation of the five weighing is no greater than 0.3 g, and each set of 15 sheets is dried for at least 16 hours at 60±2° C. and cooled to 23±3° C. in a tightly closed container with a volume that is maximally 30 times larger than the volume of the set comprising 15 sheets.

A further preferred embodiment relates to an inventive testing method in which the experimental set-up corresponds to DIN EN ISO 12863 of 2010 or DIN EN ISO 12863:2011-04 dated April 2011. The method can also be performed according to other testing methods that are designed for the use of cellulose filter papers, in particular other test methods that are based on DIN EN ISO 12863.

The present invention further relates to a kit comprising a plurality of inventive filter papers or at least a stack of 3, 10 or 15 of such filter papers, information on how the rough surface of the cellulose filter paper can be determined using the marking, and optionally an experimental procedure according to DIN EN ISO 12863 of 2010 and/or DIN EN ISO 12863:2011-04.

In the kit, the orientation of all the rough surfaces of the cellulose filter paper of a stack is preferably identical. In this way, the stack can be inserted into the testing apparatus by the testing personnel in a single step.

The kit may further provide that at least 5 or at least 10 stacks are contained therein.

Information on how the rough surface of the cellulose filter paper can be determined by means of the marking does not need to be provided in the kit if this results from the design of the marking itself, for example, if the rough surface of the filter papers bears, for example, the imprint "rough" or "upside" or equivalent terms in German, English or another language. As a precaution, even in those cases the corresponding information may nevertheless be included in the kit, for example, in printed form or on a data carrier.

EXAMPLES

Brief Description of the Drawings

The present invention will be discussed in more detail below on the basis of eight drawings and exemplary embodiments. The figures show FIG. 1 The configuration of a test chamber for assessing the ignition propensity of cigarettes in an oblique view from above, FIG. 2a, b The configuration of a substrate holder in an oblique view from above and in a sectional side view.

FIG. 3 A flow diagram of an ignition propensity test according to DIN EN ISO 12863:2011-04, FIG. 4 A flow diagram of an inventive method for marking the rough side of a filter paper (in-process method), FIG. 5 A flow diagram of an inventive method for marking the rough side of a filter paper (marking of the reel), FIG. 6 A flow diagram of an inventive method for marking the rough side of the substrate (marking of the paper sheets), FIG. 7 A flow of an inventive method for marking the rough side of the substrate (marking of the round filters) and FIG. 8a-d Various embodiments of marked filter papers according to the invention.

Figure 1:
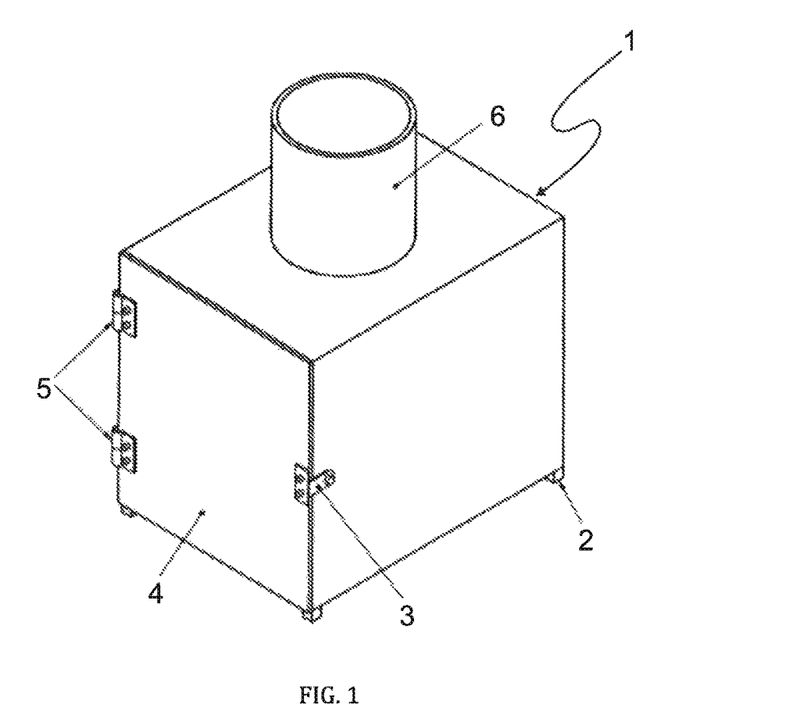

FIG. 1 shows a test chamber 1 in accordance with DIN EN ISO 12863:2011-04 for performing the inventive assessment method in an oblique view from above (source of the test chamber: DIN EN ISO 12863:1201-04). Test chamber 1 has a rectangular base and can be placed onto a surface by means of feet 2. Test chamber 1 consists of a rigid transparent material and has the dimensions of 340±25 mm in height, 292±6 mm in width and 394±6 mm in depth. The interior of test chamber 1 is accessible via a front plate 4, which is pivotally arranged on laterally arranged hinges 5, and that can be locked by a locking device 3. On the top side of test chamber 1, a smoke ventilator 6 is provided in a central arrangement having a height of 165±13 mm and an inner diameter of 152±6 mm.

Figure 2A:
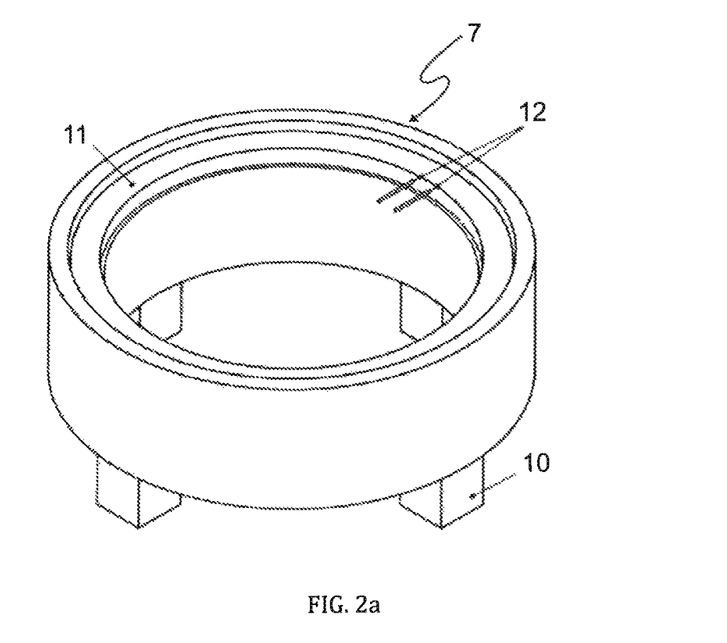
Figure 2B:
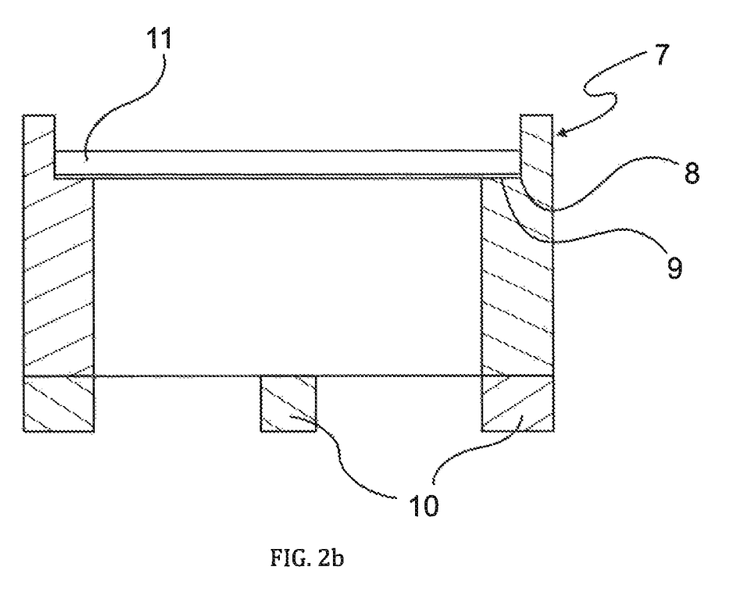

The interior space of test chamber 1 is configured to receive a cylindrical substrate holder 7 for the filter paper and for the cigarette to be tested, which is shown in FIG. 2a in an oblique view from above and in FIG. 2b in a lateral sectional view (source of the substrate holder: DIN EN ISO 12863:2011-04). At its upper edge, the substrate holder has a circumferential step (8) tapering toward the inside with a depth of 10±2.5 mm, measured from the upper edge of substrate holder 7. Step 8 is concentrically arranged and has a diameter of 152±1 mm. In this way, a stair-like protrusion is formed, the deeper area of which serves as a peripheral edge-side support 9 for the filter paper. Circumferential support 9 has a depth of approximately 25 mm.

On the underside of substrate holder 7 four feet 10 are radially arranged and equally spaced, each having a height of 20±1 mm. Substrate holder 7 has an outer diameter of 165±1 mm, an inner diameter of 127±1 mm, and a wall thickness of approximately 38 mm. The height of the substrate holder 7 without the feet 10 is 50±1 mm.

In order to fix the filter paper or the stack of filter papers, a metal ring 11 is provided which is placed from above onto the edge of the filter paper fixed in substrate holder 7. Metal ring 11 is configured as a flat ring and has an outer diameter that is smaller than the inner diameter of step 8, i.e., approximately 150±1 mm in the present case. Metal ring 11 recoils circumferentially from the inner wall of substrate holder 7 and has an inner diameter of 130±1 mm. The material thickness of metal ring 11 is approximately 6.4±1 mm. Metal ring 11 consists of brass and the metal ring 11 has a mass of approximately 270 g.

In metal ring 11, in parallel to its flat sides and approximately centrally to its cross-section, two metal pins 12 are mounted that are spaced in parallel to each other and extend approximately 17±1 mm into the interior of metal ring 11. Metal pins 12 are positioned such that an imaginary line projecting centrally and in parallel to metal pins 12 projects through the center of metal ring 11. The spacing of metal pins 12 to each other is selected such that a cigarette that is positioned between pins 12 is prevented from rolling away to the side, i.e., is fixed. Metal pins 12 are spaced approximately 8.1±1 mm apart when a conventional cigarette having a diameter of 8 mm is used.

FIG. 3 depicts a method for checking the ignition propensity of cigarette paper according to DIN EN ISO 12863: 2011-04 dated April 2011 as a flow diagram. The testing personnel must hereby first determine the rough side of the filter paper, which is generally performed manually. To this end, in the method according to the invention the inventive marked filter papers are used, which greatly simplify detecting the rough surface and almost completely rule out any errors.

The filter paper(s) is/are subsequently preconditioned. A 100-sheet box is stored with an open lid for at least seven days (7*24 h) before the test in an environment with a relative humidity of 55±5% and a temperature of 23±3° C. If filter paper stacks are used, corresponding sets, i.e., stacks of 3, 10 or 15 marked filter papers are stored for at least 8 h before the test in an environment with a relative humidity of 55±5% and a temperature of 23±3° C. The standard deviation of 5 sets comprising 15 sheets each of the conditioned marked filter paper must be 26.1±0.5 g, whereby the standard deviation of the five weighings is no greater than 0.3 g.

The actual method for checking the ignition propensity of cigarette paper is then performed in such a way that the preconditioned filter paper is placed on substrate holder 7, with the rough surface of the filter paper facing upward. Thereafter, metal ring 11 is placed on the filter paper, whereby the weight of metal ring 11 fixes the filter paper on the edge side. When filter paper stacks are used, they are pressed together by metal ring 11.

The cigarette used for the test is preconditioned before being lit by storing the cigarette for at least 24 h before the test in an environment with a relative humidity of 55±5% and a temperature of 23±3° C. This can compensate for variations in the burning behavior that might result from a possible different prestorage. Before it is lit, the test cigarette is marked with a pencil at 5±1 mm and 15±1 mm from the end of cigarettes to be lit. Subsequently, the cigarette is lit and only then placed with the seam of the cigarette paper facing upward on the rough surface of the fixed filter paper or on the filter paper stack when the glow reaches the 15±1 mm mark relative to the lit end of the cigarette. The marked cigarette is placed between metal pins 12 of metal ring 11 and fixed in this way, i.e., it is in particular prevented from rolling away.

The burning behavior of the cigarette is evaluated according to the following criteria:

A) Complete burning of the cigarette;
B) Incomplete burning of the cigarette;
C) Self-extinguishing is evaluated as A) if after being lit the cigarette extinguishes before the 15±1 mm mark of the cigarette extending from the end of the cigarette to be lit is reached, with the notation that this occurred before being placed onto the rough surface of the cellulose filter paper;
D) If the smoke of the burning cigarette is not laminar even after the chamber and the ventilation system were checked, this result is noted.

The test is repeated with at least 40 cigarettes of the same type in order to obtain a sufficient basis for a statistical evaluation of the burning behavior.

FIGS. 4 to 7 show four different embodiments of the inventive method for preparing a marked cellulose filter paper for checking the ignition propensity of cigarette paper in the form of flow diagrams.

Figure 4:
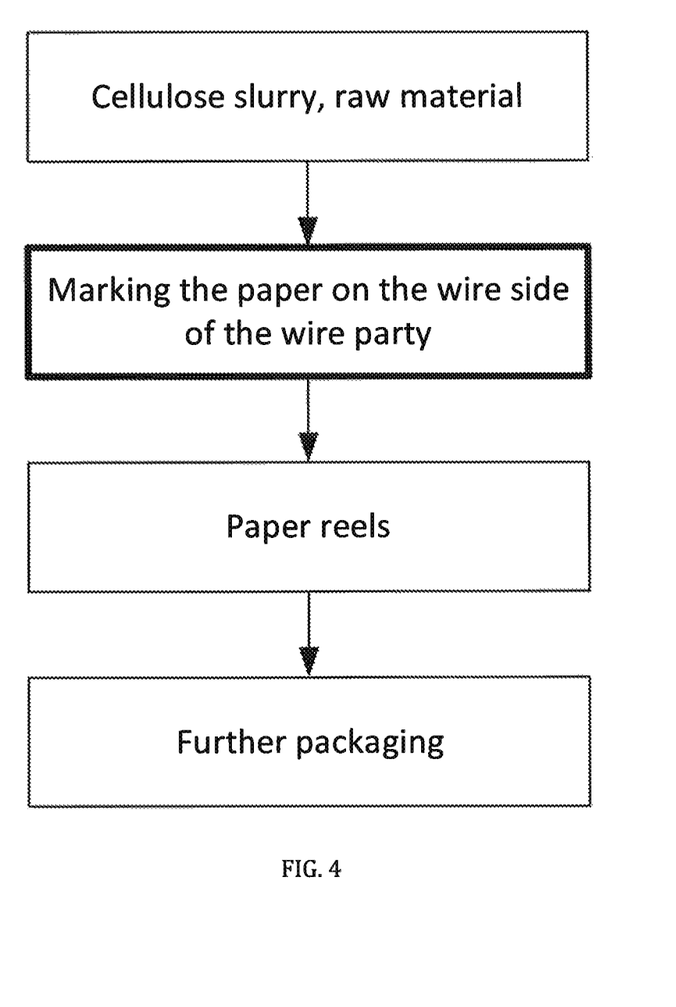

In the flow diagram depicted in FIG. 4, the filter paper is marked during the production on the wire side of the wire section, for example, by means of a true watermark. The watermarks are thereby arranged in such a manner that after passing through the entire production process up to the finished round filter paper they are arranged at the desired location of each individual filter paper.

Figure 5:
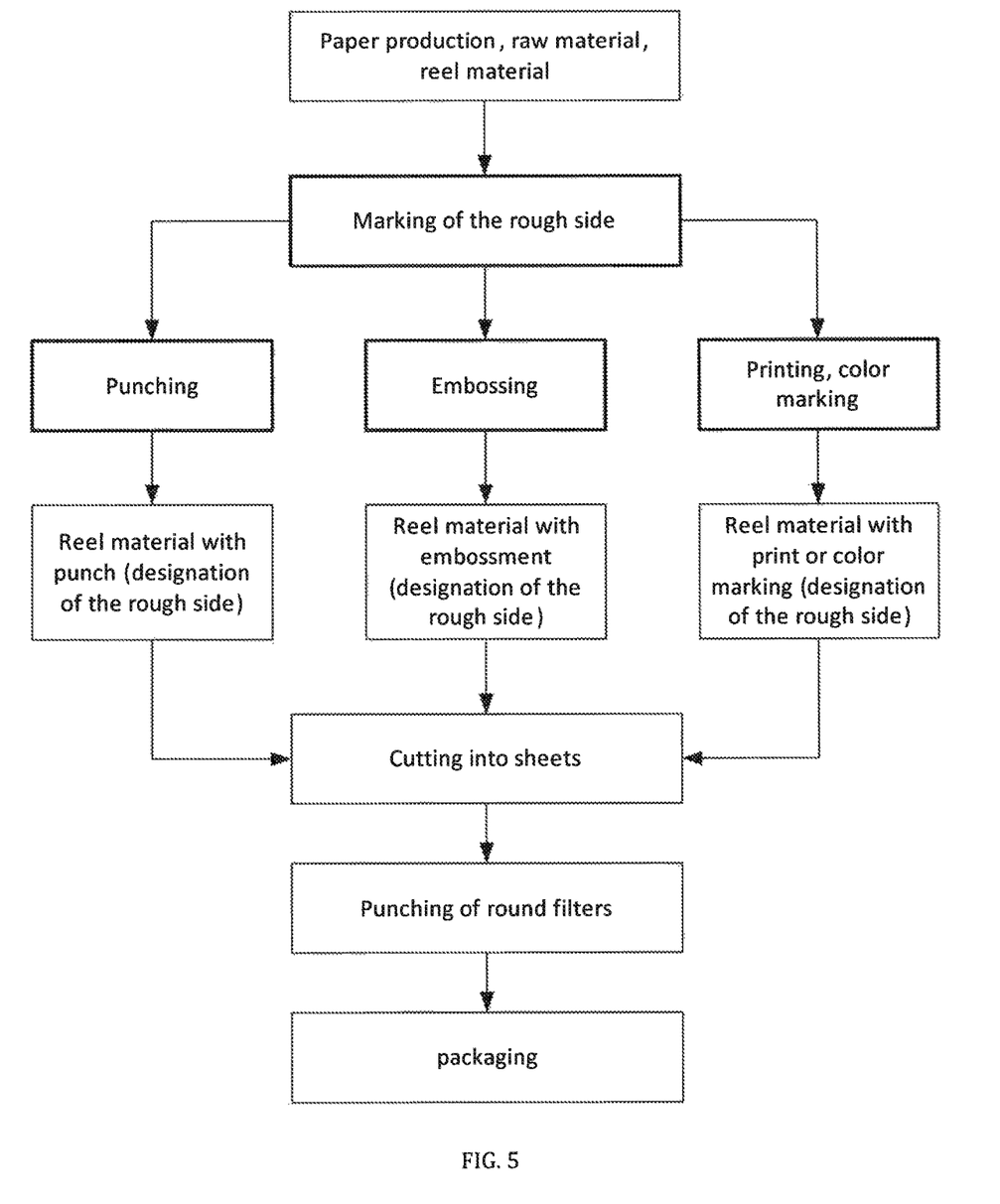

FIG. 5 shows a further option for producing the marked filter paper according to the invention. In this method, the filter paper is provided for the marking process as reel material. When reel material is used, the location of the rough surface is already known as a result of either the production process, or it can be determined once for the entire reel using a measurement method so that the orientation is known for the further production process. The marking is then applied on the reels by punching, embossing, or printing at those positions at which the marking is later desired in the finished round filter. The marked reel material is subsequently cut into sheets out of which the round filters are then punched.

Figure 6:
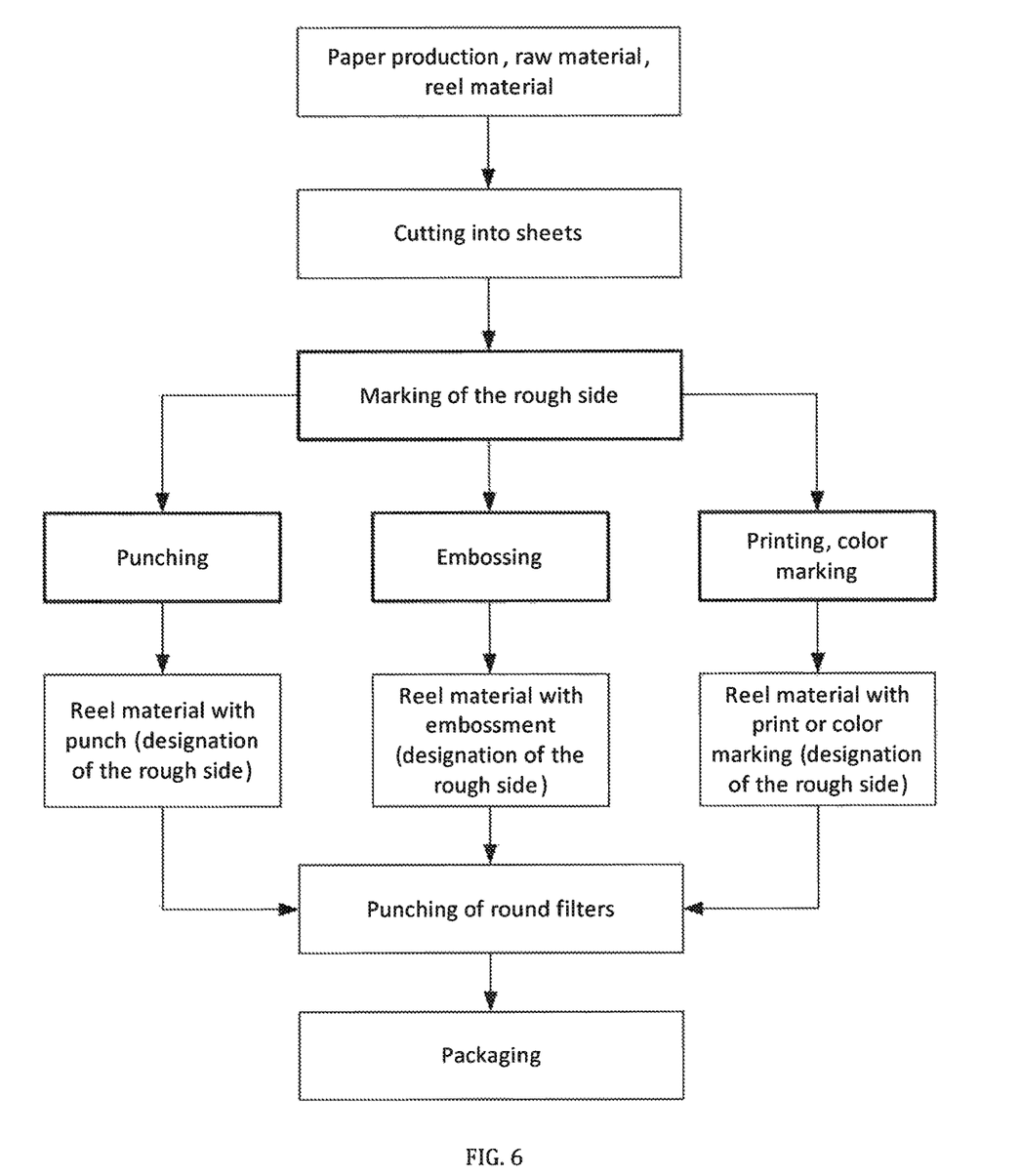

FIG. 6 depicts a flow diagram of a third embodiment of an inventive production method for marked filter papers. In this process variant, the marking takes place after the reels are cut into sheets. In this case as well, the position of the rough surface is either known from the production process or can be determined for the entire reel before it is cut into sheets. If sheets are delivered, the rough surface can be determined individually for each sheet. The respective markings are then applied to the sheets by punching, embossing, or printing at the desired position of the round filters that are subsequently generated. The round filters are then punched out of the sheets and packaged.

Figure 7:
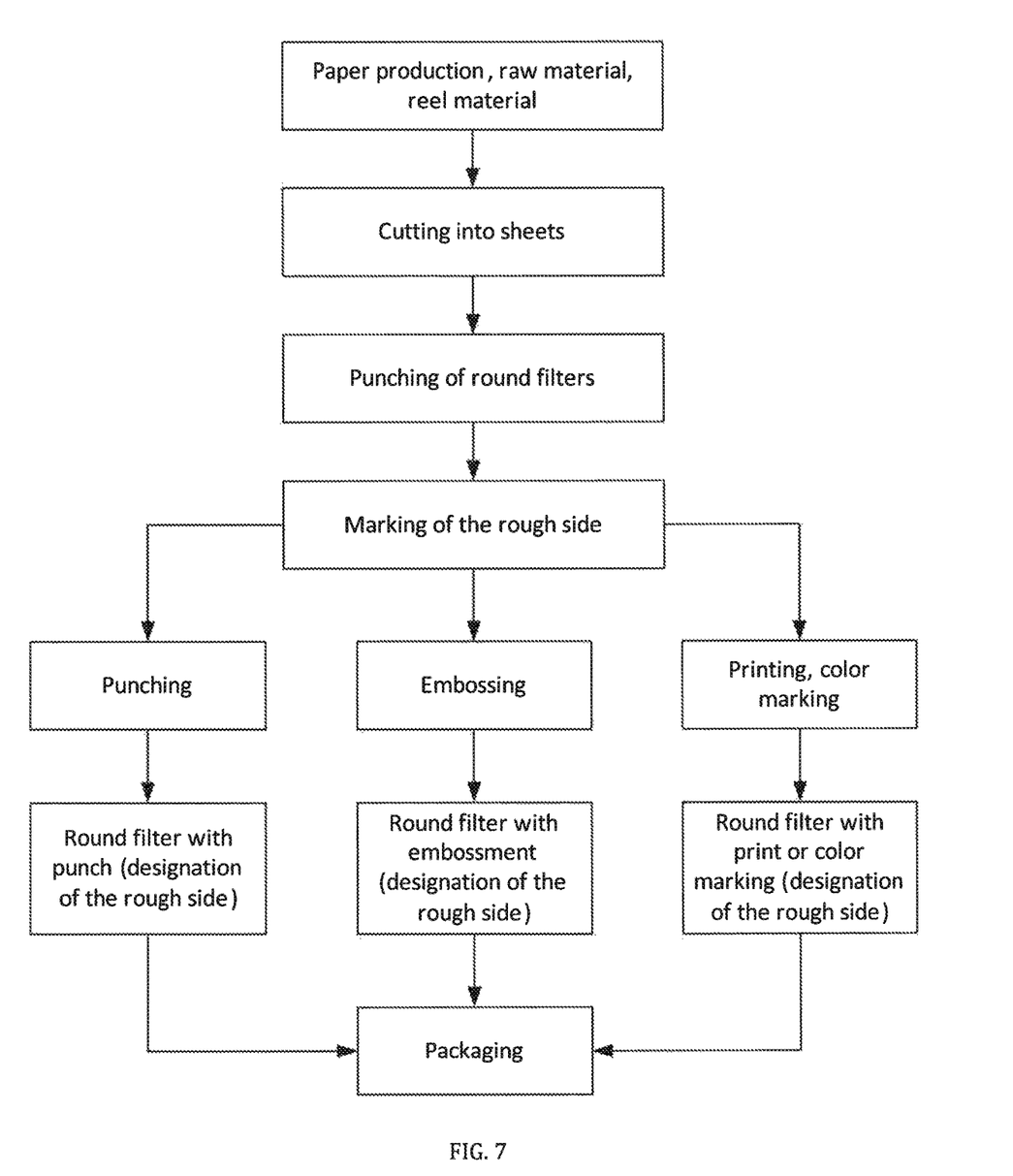

FIG. 7 depicts a fourth embodiment of an inventive manufacturing method for producing marked paper filter. In the flow diagram shown here, the filter papers are marked after they were punched out of the sheets. In this case as well, the position of the rough side of the reel material fed during the production process is known either prior to production or can be previously determined based on a single test for the entire paper reel. The marking of the punched round filter is then applied by punching, embossing, or printing. Since the position of the rough surface is known throughout the entire production process, it is not necessary in this case to determine the rough surface of each round filter prior to applying the marking. Applying the marking onto punched round filters has the advantage that the positions of the marking(s) can be defined with a higher precision than with the other aforementioned methods.

FIGS. 8a-f show different embodiments of the marked round filters marked according to the invention. In the embodiment shown in FIG. 8a, a marking "upside" is applied to the rough surface of the cellulose round filter. This can only be read from the correct side. If the marking is in principle also visible from the back side, such as is the case with a watermark or embossing, the word "upside" can be read only as a mirror image from the smooth side, so that it is easy for the testing personnel to identify the "correct" side, namely the rough surface.

Figure 8:
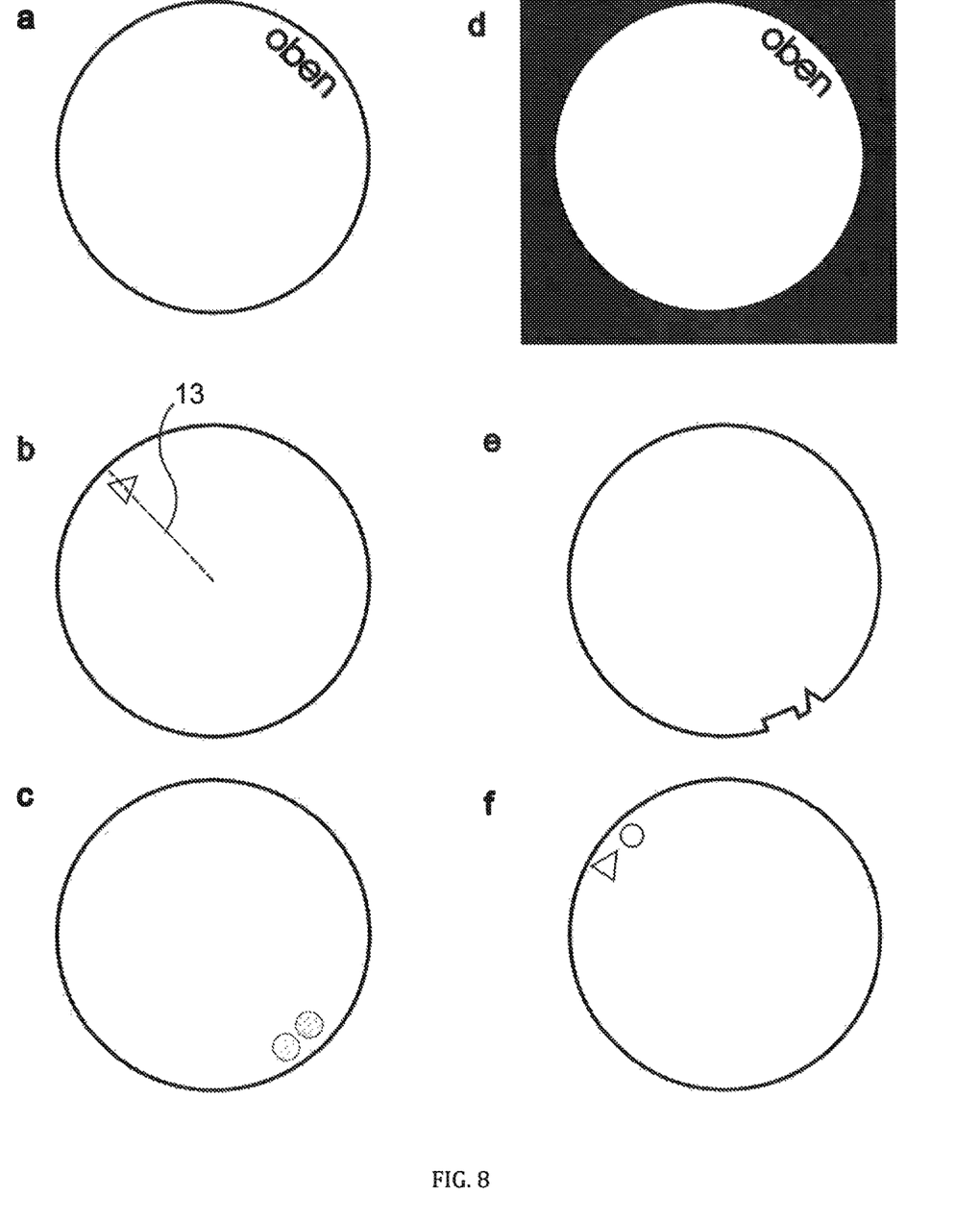

FIG. 8b shows an embodiment of a marked filter paper in which an asymmetrical symbol is applied in the form of a triangle. The asymmetry thereby arises from the fact that the symbol does not have mirror symmetry with respect to a radius line 13, which projects from the center of the round filter through the center of the marking, i.e., the triangle. In the embodiment shown in FIG. 8b, the triangle points in the clockwise direction. If this symbol is also visible from the backside of the filter paper, it would point in the anticlockwise direction in this case, and therefore, even if the marking is visible from both sides, unambiguously indicate the rough filter paper surface to the test personnel.

FIG. 8c depicts a further embodiment of the filter paper marked according to the invention in which colored symbols are printed (shown here with different shadings) that identify the rough surface of the filter paper.

In analogy to FIG. 8a, FIG. 8d depicts a marked filter paper, whereby in this case the lettering upside" was punched out of the paper. When viewing the rough side, the punched lettering appears in plain text (the background can be seen through the punch).

FIG. 8e depicts a further embodiment of a filter paper marked according to the invention. Here, geometric shapes are punched out from the edge of the filter paper, namely a rectangle and a wedge in the present case. The rough surface of the filter paper is characterized in the embodiment illustrated here in that the rectangular punch is arranged in the clockwise direction in front of the wedge-shaped punching. This embodiment also has the further advantage that in the case filter paper stacks are used, the correct assembly of each stack can be checked directly by means of the punches when the filter papers are placed on top of each other in a manner such that the punches come to lie above each other. If a filter paper were in the wrong position, it would be immediately noticeable since in that case one could not see through all the punches.

FIG. 8f depicts a sixth embodiment of a cellulose round filter paper marked according to the invention. In this embodiment, two geometric figures are applied to the round filter in the edge region, namely a triangle whose tip points to a circle that was also applied. In embodiments in which these two symbols are visible on both sides of the filter paper, the rough surface can be identified because on the rough side the circle is positioned in the clockwise direction in front of the triangle and the triangle points in the clockwise direction.

LIST OF REFERENCE NUMBERS

1 Testing chamber
2 Foot
3 Locking device
4 Front plate
5 Hinge
6 Smoke ventilation
7 Substrate holder
8 Step
9 Surface
10 Foot
11 Metal ring
12 Pin
13 Radius line

The invention claimed is:

1. Cellulose filter paper comprising a smooth surface and a rough surface to check the ignition propensity of cigarette paper, wherein the filter paper is provided with a marking with which the smooth surface of the filter paper can be distinguished from the rough surface, wherein the roughness is defined according to DIN 53108:1995-01.

2. The filter paper according to claim 1, wherein the filter paper is a single-layer round filter having a diameter in the range of from 130 mm to 170 mm.

3. The filter paper according to claim 1, wherein the marking allows to discriminate between the rough and the smooth surface of the filter paper by means of haptic sensation and/or with the normal-sighted human eye.

4. The filter paper according to claim 1, wherein the marking of the filter is located on the rough surface of the filter paper.

5. The filter paper according to claim 1, wherein the marking of the filter paper comprises a watermark, a semi-fragile watermark, an embossing, a print and/or a punch, whereby the marking is positioned in particular outside of the center point of the filter paper.

6. The filter paper according to claim 1, wherein the marking comprises a word or phrase in any language that is legible on the rough surface of the filter paper.

7. The filter paper according to claim 1, wherein the marking comprises at least two geometrical symbols that differ from each other with respect to their shape, color and/or size.

8. A method for producing the cellulose filter paper according to claim 1, wherein the filter paper is provided with a marking with which the smooth surface of the filter paper can be distinguished from the rough surface.

9. A method for checking the ignition propensity of cigarette paper comprising the steps:
  a) preconditioning a round cellulose filter paper having a rough and a smooth surface;
  b) horizontally placing the pre-conditioned filter paper onto a substrate holder, whereby the rough surface of the filter paper faces upward,
  c) subsequently placing a metal ring onto the filter paper, whereby the metal ring has two metal pins spaced in parallel to each other and which protrude into the interior of the metal ring for fixing an ignited cigarette that protrudes into the interior of the ring, and which have a spacing to each other and a length that allows an unlit end of a cigarette to be fixed;
  d) subsequently placing a cigarette ignited at one end with the seam of the cigarette paper facing upward onto the rough surface of the filter paper, whereby the non-lit end of the cigarette is fixed between the metal pins and
  e) determining the burning behavior of the cigarette, wherein the filter paper is the cellulose filter paper according to claim 1, whereby step e) is analyzed according to the following criteria:
    A) complete burning of the cigarette;
    B) incomplete burning of the cigarette,
  whereby A) means that when filter cigarettes are used a cigarette continues to burn until the front edge of the tipping paper is reached, or when cigarettes without filter are used until the metal pins are reached, and
  B) means that when filter cigarettes are used the cigarette extinguishes before the front edge of the tipping paper is reached or when cigarettes without filter are used before the metal pins are reached.

10. The method according to claim 9, further comprising:
  f) at least 39 repetitions of steps a) to e) and
  g) determining the proportion of the at least 40 tests in which the result was A).

11. The method according to claim 9, wherein a plurality of filter papers are preconditioned in step a) and a stack of the preconditioned filter papers are placed on the substrate holder in step b), whereby the rough surfaces of the filter papers of the stack face upward and the stack comprises at least 3 filter papers.

12. The method according to claim 9, wherein the preconditioning of the filter paper in step a) is performed in such a manner that a 100-sheet box containing marked filter paper is stored with an open lid for at least seven days (7*24 h) in an environment with a relative humidity of 55±5% and a temperature of 23±3° C., or sets of 3, 10 or 15 filter papers are stored for at least 8 h before the test in an environment with a relative humidity of 55±5% and a temperature of 23±3° C.

13. The method according to claim 9, wherein the method is performed according to DIN EN ISO 12863 of 2010 or DIN EN ISO 12863:2011-04.

14. The method according to claim 9, wherein a plurality of filter papers are preconditioned in step a) and a stack of the preconditioned filter papers are placed on the substrate holder in step b), whereby the rough surfaces of the filter papers of the stack face upward and the stack comprises 10 or 15 filter papers.

15. A kit comprising a plurality of cellulose filter papers according to claim 1, optionally information on how the rough surface of the cellulose filter paper can be determined by means of the marking, and optionally an experimental procedure according to DIN EN ISO 12863 and/or DIN EN ISO 12863:2011-04.

16. The kit according to claim 15, wherein the orientation of all rough surfaces of the cellulose filter papers of a stack are identical.

17. The kit according to claim 15, wherein the plurality of cellulose filter papers are arranged in at least 5 stacks are contained therein.

18. The filter paper according to claim 1, wherein the filter paper is a single-layer round filter having a diameter of 150±2 mm.

19. The filter paper according to claim 1, wherein the marking of the filter paper comprises a watermark, a semi-fragile watermark, an embossing, a print and/or a punch, whereby the marking is positioned in an edge region of the filter paper.

* * * * *